(12) United States Patent
Barnes et al.

(10) Patent No.: US 6,474,144 B1
(45) Date of Patent: Nov. 5, 2002

(54) DETERMINING THE LEVEL OF PARTICULATE CONTAMINATION IN A FLUID POWER SYSTEM

(76) Inventors: John Barnes, 15 Tuna Puna La. Coronado Cays, San Diego, CA (US) 92118; Philip Raymond John Lloyd, 721 Fourth St. Coronado, San Diego, CA (US) 92118

( * ) Notice: Subject to any disclaimer, the term of this patent is extended or adjusted under 35 U.S.C. 154(b) by 0 days.

(21) Appl. No.: 09/531,077

(22) Filed: Mar. 18, 2000

(51) Int. Cl.[7] .................. G01N 15/06; G01N 15/00; G06G 7/57; G08B 21/00
(52) U.S. Cl. .................. 73/61.71; 73/61.73; 422/73; 422/68.1
(58) Field of Search .............. 73/61.71, 61.64, 73/61.73; 422/73, 68.1

(56) References Cited

U.S. PATENT DOCUMENTS

| | | | |
|---|---|---|---|
| 3,050,987 A | 8/1962 | Osgood et al. ................. 73/61 |
| 4,181,009 A | * 1/1980 | Williamson .................. 73/61.4 |
| 4,468,954 A | 9/1984 | Lanctot et al. ............... 73/61 R |
| 4,495,799 A | 1/1985 | Fisher et al. ................. 73/61 R |
| 4,599,893 A | 7/1986 | Fisher et al. ................. 73/61 R |
| 4,663,966 A | 5/1987 | Fisher et al. ................. 73/61 R |
| 4,685,066 A | 8/1987 | Hafele et al. ................ 364/509 |
| 4,765,963 A | * 8/1988 | Mukogawa et al. .......... 422/68 |
| 4,833,909 A | * 5/1989 | Matthiessen .................... 73/23 |
| 4,941,345 A | * 7/1990 | Altemark et al. ............. 73/23.2 |
| 4,977,517 A | * 12/1990 | Gibbs, Jr. et al. ........... 364/510 |
| 5,095,740 A | 3/1992 | Hodgson et al. ............. 73/61 R |
| 5,161,406 A | * 11/1992 | Heinonen .................... 73/23.2 |
| 5,209,102 A | * 5/1993 | Wang et al. ................ 73/28.01 |
| 5,385,043 A | * 1/1995 | Fitch et al. ................. 73/61.73 |
| 5,770,152 A | * 6/1998 | Schuster et al. ............... 422/73 |

OTHER PUBLICATIONS

John Barnes & Philip Lloyd. Statement relating to the invention of a Silt Blockage Sensor for Determining the Level of Particulate Contamination in a Fluid Power System—Feb. 6, 1998.

* cited by examiner

Primary Examiner—Daniel S. Larkin
Assistant Examiner—David J. Wiggins

(57) ABSTRACT

A device for determining the level of particulate contamination in a fluid power or lubrication system. Between the inlet and the outlet of the device, working fluid passes through a narrow orifice (26) defined between a cylindrical spool (22) and surrounding sleeve (20). As the orifice becomes obstructed by particulate contamination, fluid flow through the device reduces. The contamination level is assessed by measuring the characteristic reduction in fluid flow rate over a period of time. Following the measurement cycle, fluid flow through the device is reversed causing the spool to move relatively within the sleeve to an area of increased bore (40) whereby the enlarged gap allows the release of all trapped contaminants. Following this flushing cycle, the fluid is reverted to the original flow direction, the spool returns to the position within the spool that defines the narrow orifice and another measurement cycle begins.

6 Claims, 2 Drawing Sheets

DETERMINING THE LEVEL OF PARTICULATE CONTAMINATION IN A FLUID POWER SYSTEM

CROSS-REFERENCE TO OTHER APPLICATIONS

Not applicable.

BACKGROUND—FIELD OF INVENTION

This invention relates to fluid power systems, specifically to a device for the determination of the level of solid particulate contaminants within the working fluid in a fluid power system or lubrication system.

BACKGROUND—DESCRIPTION OF PRIOR ART

Although fluid power systems and lubrication systems generally have the reputation of high reliability, the cost of a system failure can be significant, through damage, downtime and, in extremis, danger to personnel. There is overwhelming evidence that associates a fluid power system's reliability to the level of particulate contamination present in the working fluid. It has been establish,ed that clean systems suffer fewer problems with component wear, seal breakdown awl, most important, with catastrophic failures such as valve seizure. It follows that, by determining the particulate contamination level of a fluid system, component and system health can be monitored. Fluid contamination monitoring not only establishes when fluid and filters should be cleaned or replaced but, also, forecasts impending component failure—thereby allowing predictive maintenance procedures to be initiated.

One of the most common techniques for assessing fluid continuation is the Patch Test. A small sample of working fluid, previously drained from the fluid system, is forked through a filter membrane (patch). The degree of contamination is indicated by the discoloration of the patch. The problem with this procedure is that the small fluid sample is unlikely to represent overall system contamination level. Additionally, the test cannot readily distinguish particulate sizes and quantitative measurements of contamination levels (in terms of ISO, NAS, or ASTM numbers) are impossible. Finally, the procedure typically takes two hours or more and must be carried out under laboratory conditions to avoid extraneous contaminants from entering the sample during measurement.

Another common technique for contamination monitoring is based on optical counter technology. Here a beam of light (white or laser) is directed through a sample of the working fluid whereupon it impinges on a photo-detector arrangement that senses both the size and occurrence (concentration) of the particulates. Particulate counters are available as static, offline monitors (requiring a sample of fluid to be tested under laboratory conditions) or as portable on-line monitors (temporarily integrated with the fluid power system). Optical counter technology has several problems: Firstly, at high concentrations of particles, monitor response becomes saturated. Secondly, sensor collaboration is set against a standard contaminant such as AC dust or glass spherical particles; however, wear debris is rarely spherical, giving rise to spurious results. Furthermore, optical counters cannot distinguish between water and solid particlates and may report that a system is contaminated when it is not. Entrained air and translucent particles, such as quartz and glass, also cause significant problems. Finally, optical counters are delicate in construction, expensive, and are highly sensitive to vibration and pressure ripple which affect the optical light-patch and may cause anomalous readings.

A further approach utilizes sensors to measure he pressure differential across a filter medium. The level of fluid contamination is estimated by the time taken to reach a pre-determined differential as filter blockage takes place. It is a problem with this method that it is highly sensitive to changes in pressure, flow rate, viscosity and temperature in the fluid upstream from the monitor. Accordingly, some inventors have included a second reference filter assembly to provide a computer compensated output, as in U.S. Pat. No. 4,685,066 to Hafele et al (1987). This adds significantly to monitor expense and complexity. Also, filters cannot be flushed adequately for continued operation. Therefore, filters must be changed following each measurement cycle thereby confining their adaptability and increasing running costs.

To redress some of these deficiencies, U.S. Pat. No. 3,050,987 to Osgood et al (1962) assesses contamination using an on-line monitor hat passes the working fluid through a narrow orifice (gap) between two flat displaceable surfaces. When the gap blocks with particulates, one surface is forced to move in relation to the other and the nature of the resulting movement is used to assess the degree of continuation. It is an advantage of the blockage technique in that it gives a direct indication of the contamination that is likely to cause problems in fluid power systems because the sensor gap is sized to be representative of the most critical gaps in the system. However, although Osgood's method indicates the presence of contaminants, it has the problem characterized by poor repeatability because the relative movement between two blocked plates is also highly dependent upon oil viscosity, temperature, pressure fluctuations, and contaminant shape and substance The method is, therefore, highly unpredictable in nature and unlikely to give quantitative measurement of contamination level. Due possibly to these reasons and others, Osgood's method has not been commercially developed and, to our knowledge, has never been available as a marketable product.

U.S. Pat. No. 4,468,954 to Lanctot et al (1984), and U.S. Pat. No. 4,495,799 to Fisher et al (1985) again assesses contamination using the "blockage technique". The method is characterized by passing the working fluid through a narrow annular gap and using the pressure differential across the gap to trigger a counter at a pre-determined contamination level. The cycling rate of the counter is used as an indication of the particulate concentration. It is a problem with the method that pressure within a fluid power system is rarely constant and working pressure changes, machinery vibration, as well as ripple effect, would cause the counter to operate, thereby producing false readings. Working pressure changes would also cause relative movement between the two elements of the gap, thereby releasing trapped particles prematurely and causing erroneous results. Correction of the results produced by this method to compensate for such effects would require substantial additions in both complexity and cost. Due possibly to these reasons and others, Lanctot's method has not been commercially developed and, to our knowledge, has never been available as a marketable product.

U.S. Pat. No. 4,599,893 (1986), continued by U.S. Pat. No. 4,663,966, (1987) both to Fisher et al, also employ the blockage technique. These patents are characterized by the method of introducing a sample of working fluid of pre-determined volume into a cylinder (typically 1 liter) and forcing a piston, accommodating the annular gap, from one end of the cylinder towards the other. When the gap blocks, the progress of the piston is halted. The distance traveled by the piston may be used to assess fluid contamination level, This method has several problems: In order to measure at clean concentration levels (NAS 3/ASM 0), the monitor must be typically over one meter in length and weigh as much as 80 lbs., thereby severely limiting its portability and application. Furthermore, its measurement cycle time is typically over one hour, which also limits its use as a portable device. Also, the means used to communicate force to the piston to move it through the fluid is prone to flexing, tending to distort the gap thereby causing poor repeatability of results. Finally, the distance traveled by the piston is not only related to the level of contamination but, also, to the degree of force used to move the piston. This force may not be constant or repeatable over time. Due possibly to these reasons and others, Fisher's method has not been developed commercially and, to our knowledge, has never been available as a marketable product.

U.S. Pat. No. 5,095,740 to Hodgson et al (Mar 1992) is a simplification of Fisher's design (U.S. Pat. No. 4,663,966). Working fluid is passed through a filter membrane al system pressure and the volume collected therethrough. Volume to block is then read directly. Hodgson's method is characterized by poor repeatability. Filter membranes are composed of random material providing an extremely random range of cavities for trapping debris. Also, the volume of the collected fluid used to back-flush the filter is inversely proportional to the contamination level. Therefore, should the filter block quickly with highly contaminated fluid, the flushing volume available is small and unlikely to flush the membrane adequately in preparation for the next cycle; furthermore, back-flushing a filter is known not to be fully effective. Finally, unless the filters are replaced often (thereby reducing repeatability), such a method is also highly prone to membrane failure. Should the filter burst, or become permanently blocked, full system feed pressure is routed directly to the return side of the fluid power system having significant effects upon the system.

SUMMARY

In accordance with the current invention, a device for determining the level of particulate contamination in a fluid power system comprising an inlet and outlet for working fluid, a silting device to collect contaminants, and a flow rate detector adjacent to the silting device.

Objects and Advantages

Our invention employs the blockage technique and flow rate disk discrimination. Several objects and advantages of the patent invention are to provide a contaminant monitor that:

a) operates on-line as an integral part of the fluid system and in capable of continuous and uninterrupted operation;

b) provides repeatable measurements over a wide range of contamination levels and has a rapid operating cycle time since fall blockage is not necessary;

c) is compact (typically less than 20 cms.), easily portable and sufficiently rugged for field use;

d) is light (typically less than 15 lbs.) and compatible to a wide range of operational uses;

e) gives a direct indication of the solid particulate contamination most likely to cause problems (regardless of shape or substance) in a given fluid power system;

f) is unaffected by entrained air, water, vibration, and ripple;

g) is unaffected by working fluid changes or variations in fluid flow rate, viscosity or temperature;

h) is not prone to sensor gap distortions or premature release ol collected particles;

i) the flushing volume is independent to the level of contamination, thereby allowing full flushing each cycle.

Further objects and advantages are to provide a monitor that is simple and safe to use and inexpensive to manufacture; that is integrated on-line either as a permanent installation on a fluid power system or, in a form that is fully portable (hand-held); that warns when a pre-determined (but variable) contamination level is reached; that may be used in conjunction with and controlled by, a portable computer; that is sufficiently small and of low weight so as to be applicable to airborne (aircraft) use. Still further objects and advantages will become apparent from a consideration of the ensuing description and drawings.

DRAWING FIGURES

The invention will now be described, by way of example, with reference to the accompanying drawings in which.

Figure 1:
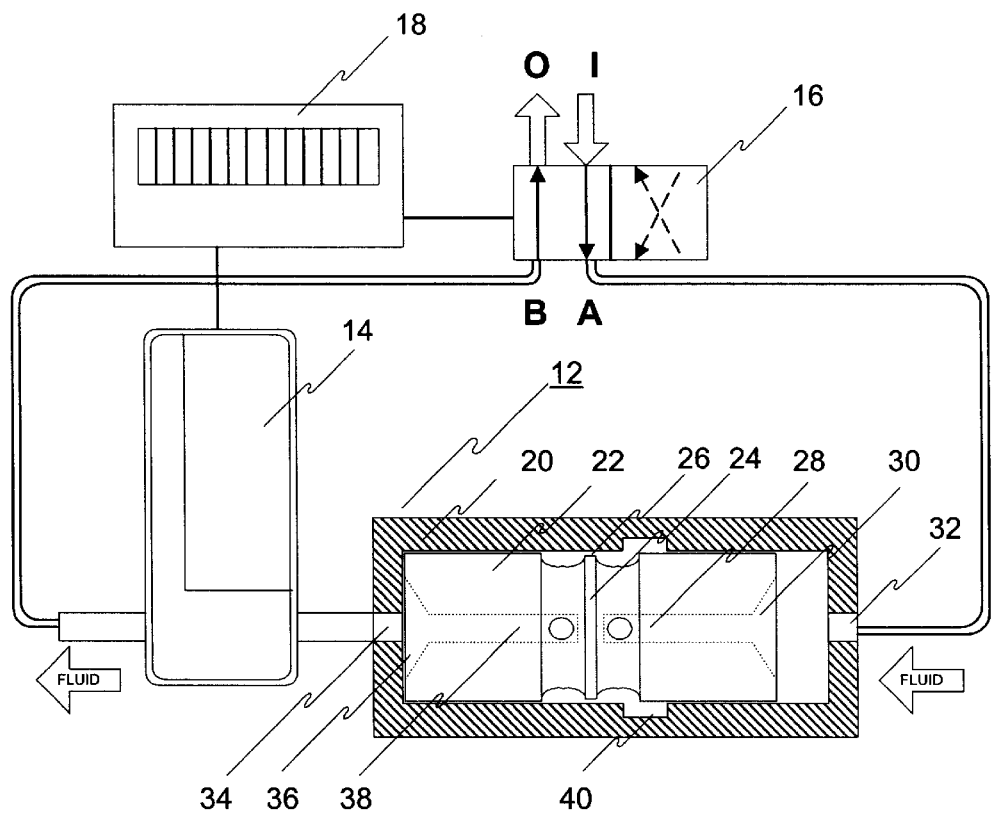
FIG. 1 is a schematic diagram showing a section through the device according to one embodiment of the design (showing the measuring cycle)

| Reference Numerals in Drawings | |
|---|---|
| 12 | Silting device |
| 14 | Flow meter |
| 16 | Control valve |
| 18 | Control/Display unit |
| 20 | Sleeve |
| 22 | Spool |
| 24 | Land |
| 26 | Orifice |
| 28 | Drilling |
| 30 | Cone |
| 32 | Drilling |
| 34 | Drilling |
| 36 | Cone |
| 38 | Drilling |
| 40 | Increased bore region |
| 42 | Device |
| 44 | Pump |
| 46 | Main Supply line |
| 48 | Low pressure return line |
| 50 | Receptacle |

DESCRIPTION

Figure 2:
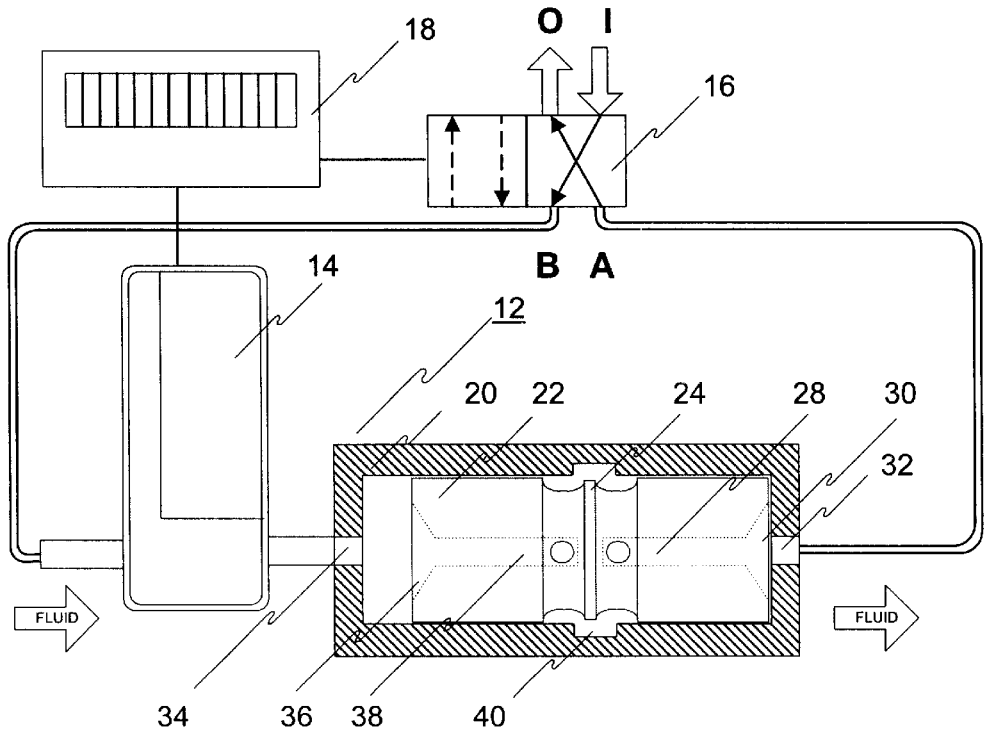
FIG. 2 is a schematic diagram showing a section through the device according to one embodiment of the design (showing the flushing cycle)
Figure 3:
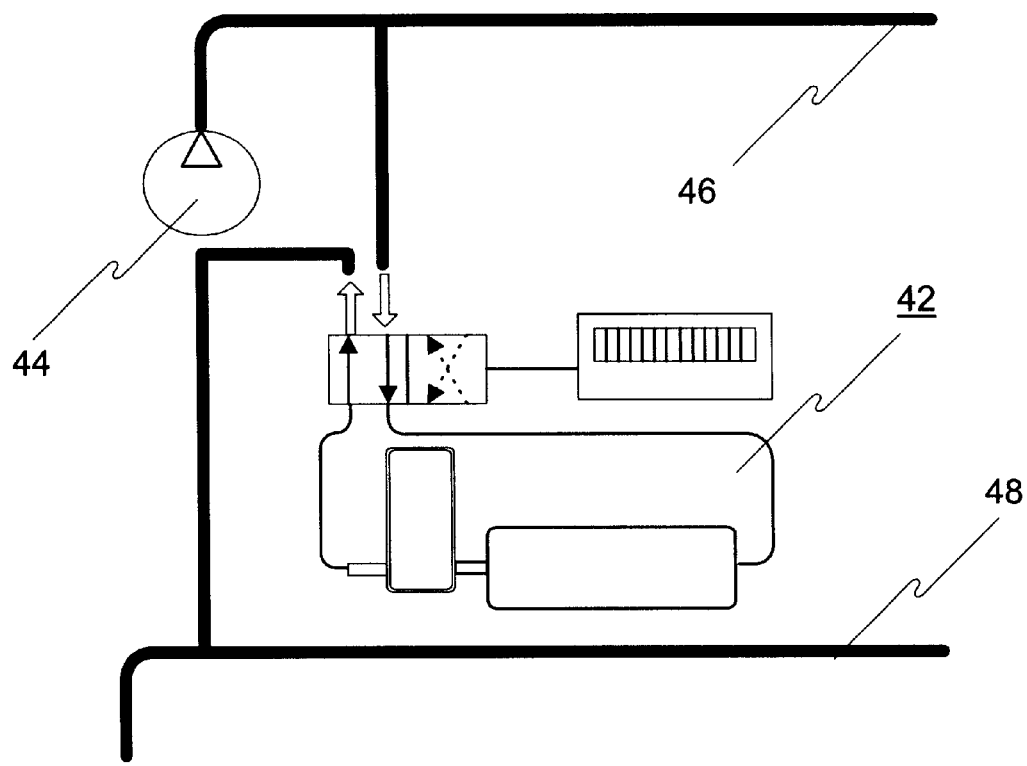
FIG. 3 is a schematic diagram showing a typical positioning of the device within a fluid power system.

FIGS. 1, 2 and 3 Preferred Embodiment

The foregoing and other objects are achieved by this invention which provides a measurement arrangement to determine the level of solid particulate contaminants within a working fluid. The contaminant monitor of this invention makes use of the known properties of a contaminant-sensitive aperture whereby the flow rate of a contaminated fluid tends to vary predictably with the accumulation of contaminants at such an aperture. This "silting characteristic" is often associated with industrial servo-valves and is normally highly undesirable; however, for the purposes of this invention, it is exploited since gives a direct indication of fluid contamination when assessed using fluid flow rate.

A preferred embodiment of the device of the present invention is illustrated in FIG. 1 (measuring cycle) and FIG. 2 (flushing cycle). FIG. 1 shows the device in its normal state. The device comprises a silting device 12 attached to a flow meter 14 each having communication with a control valve 16, and a control/display unit 18.

Silting device 12 comprises a sleeve 20 which has a hollow cylindrical interior, within which it carries a spool 22, including a land 24 which defines an orifice 26 between a the spool and the sleeve. Spool 22 is a close fit a inside sleeve 20 but may slide longitudinally within it. The critical dimension of orifice 26 is typically sized to be representative of the most critical clearances in the fluid power system (nominally within the range 5 $\mu$m to 10 $\mu$m). A drilling 28 formed in the right-band side of the spool allows axial communication of fluid between the right-band side of spool 22 and the clearance at land 24. The access to drilling 28 is in the form of a cone 30 to encourage fluid to enter spool 22 and to act as a pressure surface to facilitate moving the spool to the measuring position. Communication between control valve 16 and drilling 28 is through a drilling 32 formed in the right-hand end of sleeve 20. Similarly, a drilling 34 formed in the left-hand side of spool 22 allows axial communication of fluid between the left-hand side of the spool and the clearance at land 24. The access to drilling 34 is in the form of a cone 36 to encourage fluid to enter spool 22 and to act as a pressure surface to facilitate moving the spool to the flushing position. Communication between flow meter 14 and drilling 34 is through a drilling 38 formed in the left-hand end of sleeve 20.

Sleeve 20 is formed with an increased bore region 40 so that when spool 22 is in its flushing position (fully right) land 24 is registered with increased bore region 40 as shown by FIG. 2. When spool 22 is in its measuring position (fully left) land 24 is not registered with increased bore region 40 thereby having orifice 26 set as shown by FIG. 1.

Control/display unit 18 is electrically connected to control valve 16 to affect control and timing functions. Control/display unit 18 is also electrically connected to flow meter 14 so that when the control/display unit operates it records the instantaneous flow readings and thereafter computes and displays contamination levels through visual means. In the preferred embodiment of the invention, control/display unit 18 may incorporate an automatic timing function which may be used to cycle through sequential measuring and flushing cycles thereby allowing a plurality of measurements to be made over prolonged periods of time.

In the preferred embodiment of the invention, the contamination level of solid contaminants may be derived upon comparison with a pre-determined set of flow rate responses (signature flow rate characteristics). By comparing initial with successive flow rates (and comparing these over time with known and calibrated flow rate models) contamination levels may be established without full blockage of the orifice occurring—thereby improving response time. In another embodiment of the invention, the contamination level of solid contaminants may be derived form measuring the time between two fixed and predetermined flow rate values (initial system flow rate and zero flow rate (full blockage) for example).

For optimum results, it is desirable (but not essential) that the device of the kind shown in FIGS. 1 and 2 (referenced as 42 in FIG. 3) should be connected to the supply of the parent system fluid carrying the majority of fluid flow. In the preferred embodiment, FIG. 3, a pump 44 supplies pressurized fluid to a main supply line 46 of the parent fluid power system. A feed from this line passes directly to the inlet port of the device. The outlet port of the device is connected to a low-pressure return line 48 of the parent system and then to tank. In this configuration, continuous operation is available.

Figure 4:
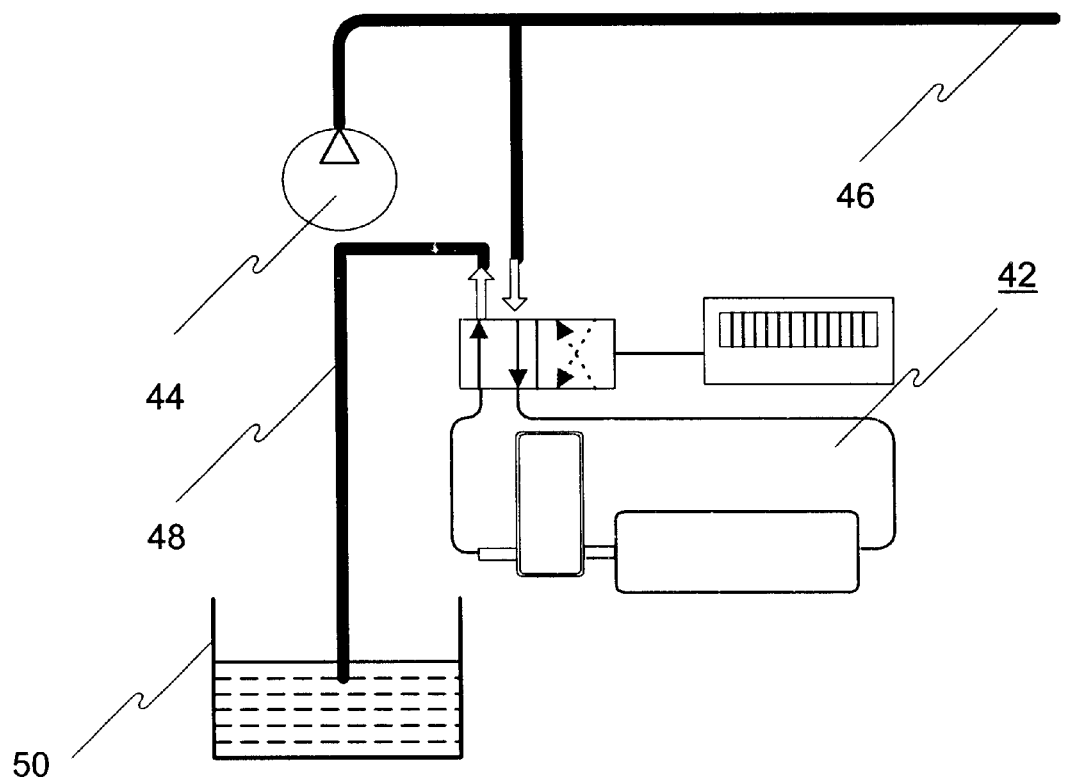
FIG. 4 is a schematic diagram showing an alternative positioning of the device within a fluid power system.

FIG. 4—Alternative Embodiment

FIG. 4 shows an alternative way to connect the device within a fluid power system. Main supply line 46 is identical to that of FIG. 3. However, the outlet port of device 42 is connected to a receptacle 50 which may have such capacity so as to bold one or a plurality of cycles of system fluid. In this configuration, access to the low-pressure line is not required and operation is possible on a small sample basis adding to the invention's portability

Advantages

From the description above, a number of advantages of our contaminant monitor become evident:

a) The orifice/flow meter configuration provides a very compact unit (typically less than 20 cms.) easily portable and sufficiently rugged for field use. Its simplicity also makes the unit very cost effective and low maintenance (there is only one moving part).

b) The orifice/flow meter configuration provides a light (typically less than 15 lbs.) monitor, making the unit highly portable and compatible with a wide variety of applications—both permanent and temporary.

c) The device may be located in a fluid power system so that it becomes an integral, on-line part, capable of continuous operation d) The orifice/flow meter configuration provides repeatable measurements over a wide range of contamination levels and has a rapid operating cycle time since full aperture blockage is not necessary.

e) The orifice/flow meter configuration provides a direct indication of the solid particulate contamination most likely to cause problems (regardless of shape or substance) in a given fluid power system.

f) The orifice/flow meter configuration is unaffected by entrained air, water, vibration, and ripple. It is also unaffected by working fluid changes or variations in flow rate, viscosity or temperature. Thereby spurious readings are avoided that could lead to unnecessary system maintenance.

g) Finally, the orifice/flowmeter configuration is not prone to sensor gap distortions or premature release of collected particles. Therefore, accurate and repeatable measurements are maintained.

Operation—FIGS. 1 and 2

FIG. 1 shows the device at initial conditions. One cycle of operation of the device begins with control valve 16 de-activated, spool 22 in the fully left position, and spool land 24 registered with sleeve 20 so that the correct orifice 26 is in effect to entrap contamination. As control valve 16 is de-activated (on command from control/display unit 18), the measuring phase is initiated permitting a proportion of the system fluid at system pressure containing solid particulates to flow between inlet I anti port A. The fluid passes into silting device 12 in the first direction via drilling 32, cone 30, drilling 28, and through orifice 26 formed between land 26 and sleeve 20. As that flow takes place, particles of contaminant present in the fluid become lodged in orifice 26 and will progressively block it thereby reducing fluid flow. Fluid exiting orifice 26, exits silting device 12 via drilling 38, cone 36, and drilling 34 to pass though flowmeter 14 where the flow rate is assessed. System pressure in the first direction is sufficient to hold spool 22 in the fully left position throughout the measuring cycle. Fluid exiting flow meter 14 is ported through control valve 16 via port B and to outlet O to tank. Should spool 22 be in the fully right position at the initiation of the measuring cycle, then system pressure exerted against cone 30 will force spool 22 to move axially within sleeve 20 to the fully left position.

At predetermined intervals of time, control/display wait 18 records the instantaneous fluid flow rate measured by flow meter 14 and, through calculation or otherwise, determines fluid contamination level (since contamination level is directly proportional to the reduction in flowrate over time). In the preferred embodiment, the control/display unit records the progressive decrease in flow rate per unit time and compares these measured values with a stored library of empirical flow/time curves, each curve representing a particular contamination level. When the measurement cycle duration has produced sufficient flow rates for a correlation to be made, the contamination level will be displayed.

When sufficient time has elapsed to allow contamination measurement, control/display unit 18 activates control valve 16 to initiate the flushing cycle.

FIG. 2 shows the device in the flushing condition. The flushing cycle of operation of the device begins with control valve 16 activated permitting a proportion of the system fluid at system pressure to flow between inlet I and port B of control valve 16. Fluid enters the silting device via flow meter 14 (now disabled). Thereafter, fluid passes through silting device 12 in the second direction through trilling 38. System pressure is exerted against the surface of cone 36 causing spool 22 to move axially within sleeve 20 to the fully right position. At the fully right position, spool land 24 becomes registered with sleeve 20 so that increased bore region 40 is in effect. As that flow takes place, system pressure flows unimpeded around exposed land 24 causing previously trapped particulates to become dislodged and flushed away through drilling 28, cone 30 and drilling 32, System pressure in the second direction is sufficient to bold spool 22 in the fully right position throughout the flushing cycle. Fluid exiting silting device 12 is ported through control valve 16 via port A and to outlet O to tank.

Although the invention has been described in terms of specific embodiments and applications, these should not be construed as limiting the scope of the invention blat as merely providing illustrations of some of the presently preferred embodiments of the invention.

Conclusions Ramifications, and Scope

Accordingly, the reader will see that the Contamination Monitor of this invention can be used to detect microscopic fluid-borne debris in fluid power systems as an integral, on-line unit. It provides continuous operation and repeatable measurements over a wide range of contamination levels and has a rapid operating cycle time since full aperture blockage is not necessary. Moreover, the unit is light, compact, easily portable and sufficiently rugged for field use. Its simplicity also makes the unit very cost effective and low maintenance, The invention provides a direct indication of the solid particulate contamination most likely to cause problems and is unaffected by entrained air, water, vibration, and tipple. It is also unaffected by working fluid changes or variations in flow rate, viscosity or temperature. In addition, the orifice/flowmeter configuration is not prone to sensor gap distortions or premature release of collected particles; thereby, spurious readings are avoided that could lead to unnecessary system maintenance. Furthermore, the Contamination Monitor has the additional advantages in that:

a) its on-line capability will obviate the need to install and remove the device during operation with the inherent risk of introducing more contaminants than were previously present;

b) its continuous operation allows the detection of contamination at the earliest opportunity thereby allowing maintenance to be timely and to avoid component failure (since failing parts themselves release contaminants into the working fluid);

c) its inherently rugged construction allows the unit to be installed directly on dynamic and vibrating machinery, such as military vehicles, simulators, and robots, with no undue effects on measuring accuracy;

d) its light weight (typically less than 15 lbs.) and small size is adaptable to airborne use where no contaminant monitor has been used before. This is particularly significant since it allows the unit to be installed on aircraft fluid power systems (including control surface hydraulic actuation systems) where contamination problems can, and have, proven fatal.

Although the description above contains may specificities, these should not be construed as limiting the scope of the invention but merely providing illustrations of some of the presently preferred embodiments of this invention. For example, the unit could be coupled to a fluid filtration rig used to scrub the working fluid and to automatically de-activate the filter system when the desired level of fluid cleanliness was achieved The flow meter may be positioned either upstream or downstream of the silting device with equal effect, or it could be bypassed throughout the flushing phase to increase flow and improve flushing effectiveness. Furthermore, the flow meter described may operate by coriolis mass, vortex displacement, or other means with the appropriate accuracy and sensitivity. The spool and sleeve configuration could be adapted so that the cones were not required or that the fluid could enter the orifice from the outside of the spool and return back though the inside of the spool (or vice versa) to reduce length and weight further. The land 24 could also be arranged to pass a "squeegee" arrangement to physically remove debris and, therefore, improve flushing performance. Although the device is designed specifically to determine the levels of contamination in fluid power systems such as hydraulic actuation systems, it is equally effective in determining contamination levels in lubrication oil systems, heavy oil and fuel oil systems, electrical transformer oil cooling systems and similar devices.

Thus, the appended claims and their legal equivalents should determine the scope of the invention, rather an the examples given.

We claim:

1. A contaminant monitor for determining the level of particulate contamination suspended in the working fluid of a fluid power system comprising:

a) an inlet means for directing said working fluid into the contaminant monitor;

b) an outlet means directing said working fluid from the contaminant monitor;

c) a fluid passage extending between said inlet means and said outlet means through which said working fluid carrying suspended particulates is passed;

d) a means for reversing flow having first and second flow states, wherein when the flow reversal means is in said first flow state, the fluid flows through said fluid passage in the first direction, and when said flow reversal means is in said second flow state, the fluid flows through said fluid passage in the second direction;

e) an orifice adapted for use to have access to said fluid passage in said first flow state, said orifice sized to cause entrapment of said suspended particulates to be sensed, wherein said entrapment causes the fluid flow rate in said first direction to reduce;

f) a means for detecting said fluid flow rate of said working fluid traversing said fluid passage in said first direction;

g) a means for flushing the entrapped particulates, said flushing means adapted for use to have access to said fluid passage in said second flow state;

h) a means responsive to said flow rate detector means for recording the occurrence of said fluid flow reduction, for setting the flow reversal means to the second flow state, and for restoring said flow reversal means to the first flow state;

i) wherein said fluid flow detector means being adapted to detect reduction in the rate of flow of said working fluid as said orifice becomes blocked by solid particulates, wherein the progressive and characteristic reduction of flow rate is used to indicate the level of particulate contaminations.

2. The contaminant monitor of claim 1 wherein said orifice is formed between first and second components capable of relative movement, said two components being a spool of circular section movable within a sleeve of similar section, said spool and said sleeve being separated by an annular clearance which constitutes said orifice.

3. The contaminant monitor of claim 2 wherein said relative movement being usable to effect flushing of said entrapped solid particulates, wherein said spool may travel longitudinally within said sleeve and having two rest positions, with the first position adapted for use to allow said spool to be aligned with said sleeve at the annular clearance to constitute said orifice, and the second position adapted for use to allow said spool to be aligned with an area of increased clearance with said sleeve, said increased clearance being of sufficient gap to allow release of particulates hitherto entrapped.

4. The contaminant monitor of claim 3 wherein said relative movement between said first and second positions is affected respectively by working fluid flow in said first and second directions.

5. The contaminant monitor of claim 1 wherein said inlet means further includes attachment to said fluid system supply line and said outlet means is attached to said fluid system return line, thereby allowing a plurality of contamination measurements to be made with the contaminant monitor as an integral part of the fluid system.

6. The contaminant monitor of claim 1 wherein said inlet means further includes attachment to said fluid system supply line and said outlet means includes attachment to a portable receptacle adapted for use to accept the fluid from a limited number of contamination measurements, this configuration thereby adding to the contaminant monitor's portability.

\* \* \* \* \*